United States Patent
Eaton et al.

[11] Patent Number: 5,951,946
[45] Date of Patent: Sep. 14, 1999

[54] COMPOSITION AND METHOD OF REMOVING ODORS

[75] Inventors: Gerald B. Eaton, Houston, Tex.; Wirot Kitkrailard, Bangkok, Thailand

[73] Assignee: Energy & Environmental International, L.C., Brookshire, Tex.

[21] Appl. No.: 09/032,865

[22] Filed: Mar. 2, 1998

[51] Int. Cl.[6] .............................. A61L 9/01; A61L 11/00; A01N 65/00
[52] U.S. Cl. ........................... 422/5; 424/76.6; 424/76.9; 424/195.1
[58] Field of Search .............................. 422/5; 424/76.5, 424/76.6, 76.7, 76.8, 76.9, 195.1

[56] References Cited

U.S. PATENT DOCUMENTS

| | | | |
|---|---|---|---|
| 620,209 | 2/1899 | Zürcher | 426/550 |
| 2,794,762 | 6/1957 | Westcott | 424/76.1 |
| 3,080,295 | 3/1963 | Goorley | 422/5 X |
| 3,649,292 | 3/1972 | Quame | 426/49 |
| 4,144,355 | 3/1979 | Rawlings et al. | 426/2 |
| 4,167,559 | 9/1979 | Michel | 424/58 |
| 4,501,730 | 2/1985 | Torii et al. | 424/76.9 |
| 4,883,651 | 11/1989 | Meyer | 424/47 |
| 4,891,215 | 1/1990 | Kato | 424/76.5 |
| 4,898,727 | 2/1990 | Osada et al. | 422/5 X |
| 5,149,534 | 9/1992 | Obayashi et al. | 424/195.1 |
| 5,240,699 | 8/1993 | Osada et al. | 424/76.9 |
| 5,298,241 | 3/1994 | Obayashi et al. | 424/76.1 |
| 5,380,521 | 1/1995 | Saihara et al. | 424/76.1 |
| 5,401,502 | 3/1995 | Wunderlich et al. | 424/195.1 |
| 5,576,006 | 11/1996 | Smith . | |
| 5,639,470 | 6/1997 | Ishibashi et al. | 424/439 |
| 5,807,587 | 9/1998 | Cox et al. . | |

FOREIGN PATENT DOCUMENTS

| | | |
|---|---|---|
| 6-157328 | 6/1994 | Japan . |
| 2296259 | 6/1996 | Japan . |

OTHER PUBLICATIONS

Ono et al, "6–Methylsulfinylhexyl isothiocyanate and its homologs . . . aureus," Biosci., Biotechnol., Biochem., abstract, 1998.

Primary Examiner—Elizabeth McKane
Attorney, Agent, or Firm—Tobor, Goldstein & Healey, L.L.P.

[57] ABSTRACT

A composition for reducing odors comprising extract derived from the plants belonging to the Zingiberales order of plants is disclosed. The odor reducing composition includes a banana plant extract derived from plants belonging to the Musa genus of plants. A method of forming the odor reducing composition and a method of reducing the odor of a substrate are also disclosed.

27 Claims, 1 Drawing Sheet

COMPOSITION AND METHOD OF REMOVING ODORS

BACKGROUND OF THE INVENTION

1. Field of the Invention

The invention relates to odor reduction, methods for reducing odors and odor reducing compositions. Preferably, the invention relates to odor reducing compositions including an extract derived from plants belonging to the Zingiberales order of plants, and more preferably from plants belonging to the Musa genus of plants, e.g., banana plants. The invention also relates to a synthetic derivative of the extract.

2. Description of Related Art

Many attempts have been made to reduce odors which are offensive or objectionable to human beings. A particular challenge, however, has been to identify an odor reducing composition for effectively reducing a variety of types of odors over long periods of time. For example, some materials "mask" the odor only temporarily, and for a short period of time. In one attempt, a fragrant substance was used to mask the offending odor. The fragrant substance was, however, limited in its masking ability and ability to cope with strong odors over long periods of time. In another attempt, a composition designed to chemically react with the offending odor was defective because it required the selection of different chemicals depending on the type of odor. Without the correct chemical formulation, the odor was not reduced. Selecting the appropriate chemical formulation to treat various odors was complex, and required the preparation of numerous different odor reducing compositions depending on the offending odor. Accordingly, it is an object of the present invention to provide an odor reducing composition which reduces the odor of various types of odorous substrates for extended periods of time.

SUMMARY OF INVENTION

In one embodiment, the invention relates to a method of reducing the odor emitted by an odorous substrate by applying to the odorous substrate an odor reducing composition that includes banana plant extract. In a further embodiment, the odor is being emitted from manure, urine, fecal matter or sewage sludge. In still a further embodiment, the odorous substrate is selected from the group consisting of manure, urine, sewage sludge, hay, straw, grass, soil, compost, carpet, animal feeds, diapers, garbage, food wastes, ponds, fountains, and septic tanks. In an additional embodiment, the odor reducing composition is sprayed onto the manure. In yet a further embodiment, the odor reducing composition is applied to the sewage sludge in an amount of from about 0.5% to about 15% based on the volume of the sewage sludge.

In another embodiment, a method of reducing the odor of an odorous substrate by applying an odor reducing composition including banana plant extract includes the steps of providing an odorous substrate; and applying to the odorous substrate an odor reducing composition including banana plant extract. The odor reducing composition including banana plant extract is formed by the steps of providing a banana plant material; and removing liquid banana plant extract from the banana plant material to form the odor reducing composition. In a further embodiment, the odor reducing composition is applied to the odorous substrate in an amount sufficient to reduce the odor of the odorous substrate.

In still another embodiment, the method of reducing the odor of an odorous substrate by applying to the odorous substrate an odor reducing composition including banana plant extract includes the step of applying to the odorous substrate an odor reducing composition including banana plant extract. The odor reducing composition is formed by the steps of processing banana plant material to form a banana plant pulp. The banana plant pulp is combined with water and an alkali metal hydroxide, such as sodium hydroxide, to form a banana plant pulp mixture. The banana plant pulp mixture is heated to provide a banana plant extract mixture having a banana plant extract portion and a banana plant residue portion. The banana plant extract portion of the banana plant extract mixture can be separated from the banana plant residue portion of the banana plant extract mixture to form an odor reducing composition including banana plant extract.

In another broad embodiment, the present invention relates to a method of forming an odor reducing composition, including the steps of providing a banana plant material; and removing liquid banana plant extract from the banana plant material to form an odor reducing composition including the banana plant extract.

In another embodiment, the method for forming an odor reducing composition includes the steps of combining the banana plant material with water to form an aqueous banana plant material. The alkalinity of the aqueous banana plant material is preferably increased by adding an alkali metal hydroxide to form a banana plant mixture. The banana plant mixture is then preferably heated to form an odor reducing composition including the banana plant extract. In a further embodiment, the banana plant mixture has a pH of from at least about 9 to about 14. Preferably, the pH of the banana plant pulp mixture is from at least about 10.5 to 13. In still a further embodiment, the alkali metal hydroxide is sodium hydroxide.

In still another embodiment, the method of forming an odor reducing composition includes the steps of combining the banana plant material with water and an alkali metal hydroxide, such as sodium hydroxide, to form a banana plant mixture. The banana plant mixture is then heated to form an odor reducing composition including the banana plant extract.

In yet another embodiment, the method of forming an odor reducing composition includes the steps of processing banana plant material to form a banana plant pulp. The banana plant pulp is combined with water and an alkali metal hydroxide, such as sodium hydroxide, to form a banana plant pulp mixture. The banana plant pulp mixture is then heated to provide a banana plant extract mixture having a banana plant extract portion and a banana plant residue portion. The banana plant extract portion of the banana plant extract mixture is separated from the banana plant residue portion of the banana plant extract mixture to form an odor reducing composition including banana plant extract.

In still another embodiment, the method of forming an odor reducing composition includes the steps of grinding the banana plant material to form a banana plant pulp. The banana plant pulp is combined with water and an alkali metal hydroxide, such as sodium hydroxide, to form a banana plant pulp mixture. The banana plant pulp mixture is then heated at a temperature of at least about 80 to about 212° F. for a period of time sufficient to provide banana plant extract mixture having a banana plant extract portion and a banana plant residue portion. The banana plant extract portion of the banana plant extract mixture is separated from the banana plant residue portion of the banana plant extract mixture to form an odor reducing composition including banana plant extract. In a further embodiment, the banana plant pulp mixture is heated at a temperature of at least about 80 to 212° F. for at least about 1 to about 3 hours.

In still another broad embodiment, the invention relates to an odor reducing composition including a banana plant extract. In a further embodiment, the odor reducing composition includes a biostat, such as glutaraldehyde. In another further embodiment, the composition includes an inorganic phosphate compound, such as dibasic sodium phosphate.

In another embodiment, the invention relates to an odor reducing composition including banana plant extract, wherein the banana plant extract is formed by the steps of providing a banana plant material and removing liquid banana plant extract from the banana plant material to form an odor reducing composition including the banana plant extract.

In still another embodiment, the invention relates to an odor reducing composition including banana plant extract, wherein the odor reducing composition including banana plant extract is formed by the steps of combining the banana plant material with water and an alkali metal hydroxide, such as sodium hydroxide, to form a banana plant mixture. The banana plant mixture is then heated to form an odor reducing composition including the banana plant extract.

In yet another embodiment, the invention relates to an odor reducing composition including banana plant extract, wherein the odor reducing composition including banana plant extract is formed by the steps of processing banana plant material to form banana plant pulp. The banana plant pulp is combined with water and an alkali metal hydroxide, such as sodium hydroxide to form a banana plant pulp mixture. The banana plant pulp mixture is then heated to provide a banana plant extract mixture having a banana plant extract portion and a banana plant residue portion. The banana plant extract portion of the banana plant extract mixture is separated from the banana plant residue portion of the banana plant extract mixture to form an odor reducing composition including banana plant extract.

In still another broad embodiment, the invention is directed to an odor reducing composition including an odor reducing agent. In a further embodiment, the odor reducing composition includes a biostat, such as glutaraldehyde. In still a further embodiment, the odor reducing composition includes an inorganic phosphate compound, such as dibasic sodium phosphate or trisodium phosphate.

DETAILED DESCRIPTION AND SPECIFIC EMBODIMENTS

Figure 1:
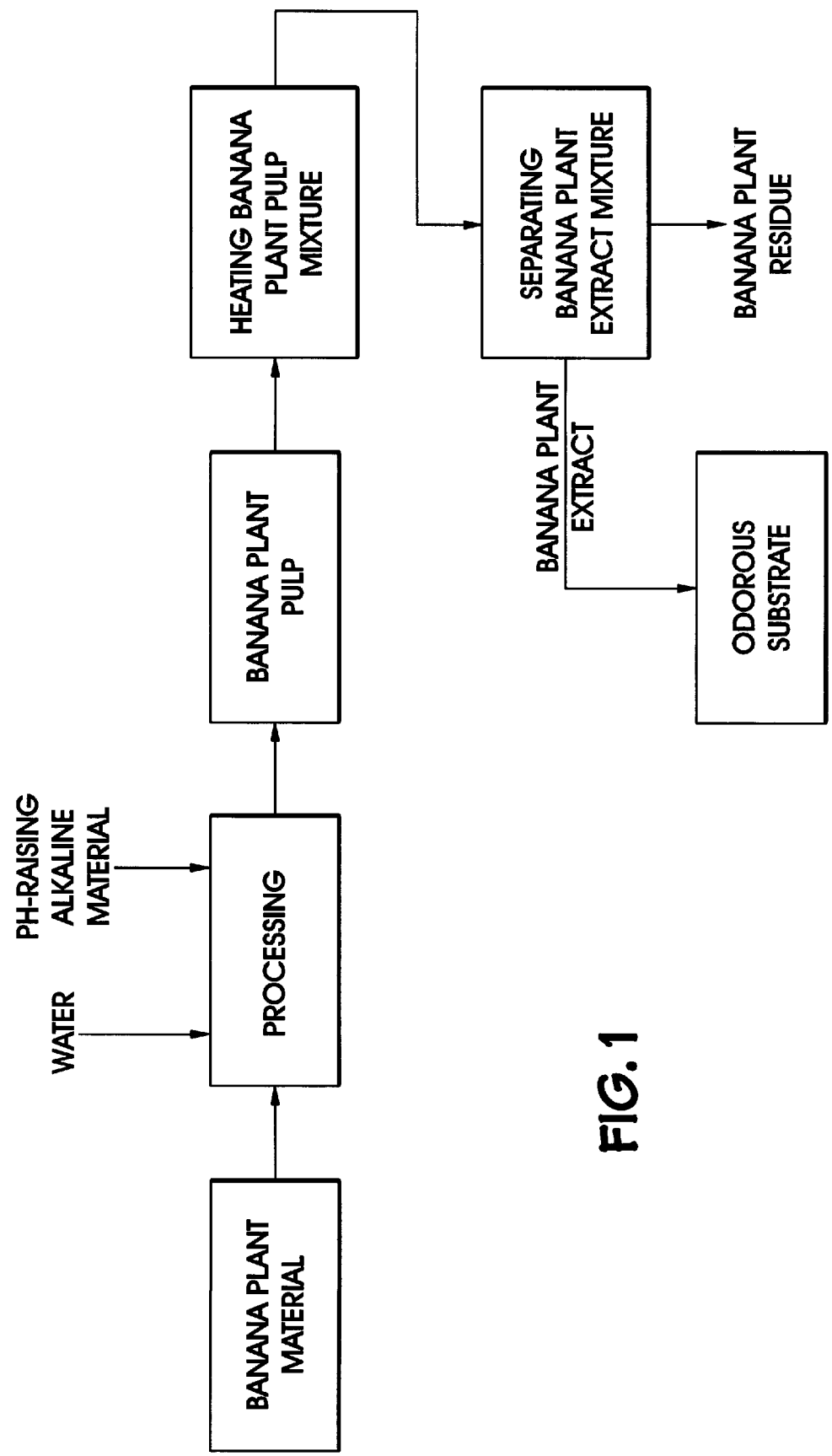
FIG. 1 is a flow chart of a method that is a specific embodiment of the present invention.

As discussed above, the present invention relates to a method of removing or reducing odors. "Removing" is herein defined as eliminating or ending the intensity, duration, and offensiveness of an odor or smell such that the odor or smell is substantially undetectable by human beings. "Reducing" is herein defined as lessening the intensity, duration, and offensiveness of an odor or smell such that the odor or smell is at least marginally eliminated. Preferably, the method involves use of an odor reducing composition that includes an extract derived from plants belonging to the Zingiberales order of plants. The invention also includes a method of forming the odor reducing composition. Advantageously, the odor reducing composition is non-toxic and biodegradeable. Accordingly, the odor reducing composition may be applied to grass and other organic materials which may be eaten by animals without causing harm to the animals or the environment.

In a specific embodiment, the present invention includes a method of forming an odor reducing composition. The method includes the steps of providing a banana plant material and removing liquid banana plant extract from the banana plant material to form an odor reducing composition that includes the banana plant extract. The odor reducing composition preferably has a pH from at least about 7 to about 14. More preferably, the odor reducing composition has a pH from at least about 9 to about 13 and even more preferably, from at least about 10 to about 12.5.

Broadly, a "banana plant material" is herein defined as including any plant in the Zingiberales order of plants, preferably in the Musacaeae family of plants, and more preferably in the Musa genus of plants. "Banana plant material" includes the non-fruit portion of the plant, including the stalks and leaves, and includes both the solid, cellulosic portion of the plant that provides structure and support, as well as the liquid portion, or juice, of the plant.

"Banana plant extract" is herein defined as a liquid portion from the banana plant material after it has been isolated from the banana plant material in accordance with this invention. The banana plant extract includes the odor reducing agent, and may also include other components such as water. "Banana plant extract" also includes any synthetically developed odor reducing agent having the same properties and characteristics as the odor reducing agent found naturally in the banana plant material, and preferably having the same or similar chemical composition as that in the banana plant extract isolated from the banana plant material. Preferably, however, the banana plant extract is isolated from the banana plant material, i.e., the banana plant extract is natural.

Referring now to FIG. 1, in another specific embodiment, the invention is directed to a method of forming an odor reducing composition. That method includes the steps of providing a banana plant material, then processing the banana plant material to form a banana plant pulp. The banana plant pulp is preferably combined with water prior to, during, or after processing. Preferably, the banana plant pulp is also combined with a pH-raising alkaline material, e.g., an alkali metal hydroxide or an alkaline earth metal hydroxide, preferably sodium hydroxide, to form a banana plant pulp mixture with an alkaline pH. The banana plant pulp mixture is heated to provide a banana plant extract mixture having a liquid banana plant extract portion and a solid banana plant residue portion. The banana plant extract portion is then preferably separated from the banana plant residue portion, e.g., by passing the banana plant extract mixture through a colander screen, to form an odor reducing composition that includes banana plant extract. The banana plant extract is then applied to an odorous substrate.

"Processing" is herein defined broadly as applying physical pressure or force, including crushing, grinding, crunching, chopping, pulverizing, mashing, pressing, thrashing, shredding, compressing, pulping, smashing, squashing or any other method in which the interior of the cellulosic material is exposed to the environment. Processing the banana plant material provides a banana plant pulp, which when combined with water and a pH-raising alkaline material, provides a banana plant pulp mixture.

Preferably, sufficient water is added to a banana plant material to provide an aqueous banana plant mixture that has from at least about 2 weight percent to about 50 weight percent banana plant material based upon the total weight of the aqueous banana plant mixture. More preferably, the banana plant material occupies from about 18 weight percent to about 25 weight percent of the aqueous banana plant mixture. Water preferably occupies from at least about 50 weight percent to about 98 weight percent based upon the total weight of the aqueous banana plant mixture. More preferably, the water occupies from about 70 weight percent to about 85 weight percent of the aqueous banana plant mixture.

After the water is combined with the banana plant material to form an aqueous banana plant mixture, the pH of the aqueous banana plant mixture may be increased by adding a pH-raising alkaline material. It is contemplated that the increased pH promotes, enhances or improves the isolation of the banana plant extract by promoting, enhancing, or causing extraction of the liquid portion of the banana plant extract mixture. Preferably, the pH-raising alkaline material is an alkali metal hydroxide or an alkaline earth metal hydroxide. More preferably, it is sodium hydroxide, calcium hydroxide, potassium hydroxide or magnesium hydroxide, either alone or in combination with one another. Even more preferably, the pH-raising alkaline material is sodium hydroxide. It is contemplated, however, that other pH-raising alkaline materials can be added instead of alkali metal hydroxides and alkaline earth metal hydroxides. In one specific embodiment, calcium hydroxide and sodium hydroxide are used in combination with one another. The presence of the calcium hydroxide reduces the concentration of sodium in the odor reducing composition and provides an odor reducing composition which, by the presence of calcium, functions as a soil amendment or fertilizer additive. This embodiment may be applied to manure which may ultimately be used as a fertilizer or fertilizer additive.

The pH-raising alkaline material should be added to the aqueous banana plant material to form a banana plant mixture in an amount ranging from at least about 0.05 weight percent to about 5.0 weight percent based upon the total weight of the banana plant mixture, e.g., the banana plant material, water and pH-raising alkaline material. Preferably, the banana plant material has been, or is being, processed so that the banana plant material forms a banana plant pulp which, by addition of water and the pH-raising alkaline material forms a banana plant pulp mixture.

When a banana plant mixture (which is preferably a banana plant pulp mixture) is formed, the pH-raising alkaline material is preferably present in an amount ranging from at least about 0.1 weight percent to about 1.0 weight percent based upon the total weight of the banana plant mixture. As a result of the addition of the pH-raising alkaline material, the pH of the banana plant mixture is preferably increased to at least about 9 to about 14. Surprisingly, it has been discovered that if the pH of the banana plant mixture is not raised to at least about 9, the effectiveness of the odor reducing composition in reducing odors is less than satisfactory. On the other hand, if the pH of the banana plant mixture or banana plant pulp mixture is above 14, a highly caustic compound is formed which may be dangerous to store and use and provides no increase in the effectiveness of the odor reducing composition to reduce odors. The most preferred pH of the banana plant mixture is at least about 10.5 to about 13.

The pH of the banana plant mixture, containing both solids and liquids, is preferably maintained at about 10.5 to about 13 for an amount of time sufficient for the banana plant extract to be extracted from the banana plant mixture and into the banana plant extract mixture. As discussed above, the banana plant mixture is preferably a banana plant pulp mixture. While any method known to persons skilled in the art may be employed to facilitate the extraction of the banana plant extract from the banana plant mixture, the preferred method is processing the banana plant material to form a banana plant pulp, combining the banana plant pulp with water and a pH-raising material to form a banana plant pulp mixture, and heating the banana plant mixture. The banana plant mixture should be heated at a temperature of from at least about 80 to about 212° F. for a period of time sufficient to provide a banana plant extract mixture. The banana plant extract mixture includes a solid portion, which is primarily the banana plant residue, and a liquid portion, which is primarily the banana plant extract. Heating the banana plant pulp mixture causes the banana plant extract to be extracted out of the banana plant pulp mixture at an effective rate. Preferably, a banana plant pulp mixture is heated at a temperature of about 212° F. for at least about 1 hour to about 3 hours. More preferably, a banana plant pulp mixture is heated at a temperature of about 212° F. for about 2 and one-half hours. After the banana plant pulp mixture is heated, so that banana plant extract mixture is formed, the liquid banana plant extract may be separated from the solid banana plant residue.

Separating the liquid banana plant extract portion from the solid banana plant residue portion may be accomplished by any method known by persons skilled in the art. For example, the banana plant extract mixture may be passed through a wire mesh, or colander screen, having openings such that all, or substantially all, of the solid banana plant residue portion is removed from the banana plant extract mixture. Preferably, the entire solid banana plant residue portion of the banana plant extract mixture is removed. Pressure may be applied during the separation step to enhance the separation of the banana plant extract from the banana plant residue. Separation of the banana plant extract portion from the banana plant residue portion may also be accomplished using a hydrocyclone or a centrifuge. Preferably, the banana plant extract portion is separated from the banana plant residue portion using a colander screen. The banana plant extract portion is then useful for being applied to odorous substrates as an odor reducing composition.

The banana plant extract is preferably applied directly to the odorous substrate in its liquid form after its isolation as the odor reducing composition. Further, dilution of the banana plant extract, however, may be appropriate for some applications to odorous substrates. For example, water may be used to dilute the banana plant extract to facilitate the odor reducing composition's application using a spray bottle. The water increases the flowability of the odor reducing composition, thereby allowing easy use with a spray bottle.

In a specific embodiment of the invention, one or more inorganic phosphate compounds may be added to the banana plant pulp mixture or may be included as part of the odor reducing composition after its formation. It is contemplated that inclusion of the inorganic phosphate compounds provide an odor reducing composition having insect repellant properties. Accordingly, the odor reducing composition may be applied to manure to reduce the odor of the manure as well as to prevent the attraction of flies and other insects to the manure. The preferred inorganic phosphate compounds include metal phosphates, such as trisodium phosphate, calcium phosphate and dibasic sodium phosphate. More preferably, the inorganic phosphate compound is dibasic sodium phosphate. The inorganic phosphate compounds are preferably added to the banana plant pulp mixture in an amount ranging from at least about 0.01 weight percent to about 0.4 weight percent based upon total weight of the banana plant pulp mixture. More preferably, the inorganic phosphate compounds are added to the banana plant pulp mixture in an amount ranging from at least about 0.04 weight percent to about 0.18 weight percent based upon the total weight of the banana plant pulp mixture.

In another specific embodiment of the invention, an odor reducing composition includes an inorganic phosphate compound at a concentration ranging from at least about 0.01 weight percent to about 0.4 weight percent based upon the total weight of the odor reducing composition. Preferably, the inorganic phosphate compound is included in the odor reducing composition at a concentration ranging from at least 0.04 weight percent to about 0.18 weight percent based upon the total weight of the odor reducing composition. The inorganic composition is more preferably added to the banana plant extract after its isolation from the banana plant residue.

In still another specific embodiment of the invention, an odor reducing composition includes a preservative or biostat to prolong the useful life of the odor reducing composition. The preservative kills or inhibits growth of microorganisms such as bacteria, molds, fungi, and slimes. Preferred preservatives include antioxidants, fungicides, aldehydes, and halogen releasing compounds. The even more preferred preservatives include glutaraldehyde, 5-chloro-2-methyl-4-isothiazolin-3-one, and 2-methyl-4-isothiazolin-3-one, used alone or in combination with one another. The preservative is preferably included in the odor reducing composition at a concentration ranging from at least about 0.05 weight percent to about 10 weight percent based upon the total weight of the odor reducing composition. More preferably, the preservative is included in the odor reducing composition at a concentration ranging from at least about 0.25 weight percent to about 4 weight percent based upon the total weight of the odor reducing composition. The preservative is even more preferably added to the banana plant extract after its separation from the banana plant residue. It is contemplated that other preservatives may be included in the odor reducing composition based upon the specific application of the odor reducing composition. For example, any food preservative known to persons skilled in the art may be included in the odor reducing composition to be digested by animals.

In yet another specific embodiment of the invention, an odor reducing composition includes a surface tension reducer or wetting agent which causes the odor reducing composition to penetrate more easily into, or to spread over the surface of, an odorous substrate by reducing the surface tension, thereby enhancing the contact between the odor reducing composition and odorous substrate. The surface tension reducer may also include surfactants and/or detergents. While it is contemplated that any surface tension reducer or wetting agent may be included in the odor reducing composition, the preferred surface tension reducer is trisodium phosphate.

The surface tension reducer is preferably included in the odor reducing composition at a concentration ranging from at least about 0.01 weight percent to about 0.4 weight percent based upon the total weight of the odor reducing composition. More preferably, the surface tension reducer is added to the odor reducing composition at a concentration ranging from at least about 0.04 weight percent to about 0.18 weight percent based upon the total weight of the odor reducing composition.

In another specific embodiment, the invention includes a method of reducing the odor of an odorous substrate by applying to the odorous substrate an odor reducing composition that includes banana plant extract, including any of the odor reducing compositions discussed above. The method includes the step of applying to an odorous substrate an odor reducing composition that includes banana plant extract. The odor reducing composition can be formed by the steps of providing a banana plant material, and removing liquid banana plant extract from the banana plant material to form the odor reducing composition. The term "applying" is defined herein broadly to mean spraying, dispersing, scattering, mixing, blending, combining, stirring, merging, mingling, or any other method of placing the odor reducing composition in contact with the odorous substrate.

"Odorous substrate" is herein defined as any solid or liquid that emits an odor or smell that is desired to be reduced or eliminated, particularly odors that are widely considered to be offensive or objectionable to human beings. Examples of odorous substrates include organic solids such as hay, straw, grass and manure or fecal matter; and inorganic materials such as soil. Often, the organic and inorganic substrates are mixed or blended. The organic or inorganic materials are typically found in places such as barns, stables, chicken coops, pig sties, dog pounds, pet clinics, animal laboratories, or any other area occupied by livestock and contaminated by manure, or fecal matter, and/or urine.

Most odors identified as objectionable to human beings are the result of volatile compounds generated during the decomposition of manure. Many odorous compounds are a result of biological reactions occurring primarily in an anaerobic environment because many of the odorous compounds commonly found in fresh manure become more concentrated during anaerobic decomposition. Some of the odors emanating during the decomposition of manure are also the result of biological processes carried out during aerobic decomposition. Such odors are especially prevalent in sewage sludge retaining basins and lagoons which are aerated.

Odors originating from manure are a result of a broad range of odor producing compounds. Over 200 odor generating compounds have been identified. Commonly reported odorous compounds associated with manure and waste water are gases which are released from the manure during decomposition such as those containing sulfur, e.g., hydrogen sulfide; those containing nitrogen in the amine form, e.g., ammonia; mercaptan; volatile organic acids; phenols; and alcohols. Some of these odorous compounds have determinable points at which the odors effect human beings. For example, ammonia present at a concentration of 10 ppm may cause irritation to eyes and nose; and hydrogen sulfide present at a concentration of 10 ppm is toxic and may cause headaches, dizziness, nausea, unconsciousness, and death. The wide range of odorous compounds from manure add to the complexity of odor control solutions. The odor reducing composition of the invention works especially well in reducing the odors emanating from manure as a result of anaerobic and aerobic decomposition of the manure. It is contemplated that the odor reducing composition of the invention counteracts the gases which are being emitted by the manure by decreasing the concentration of the gases that are emitted by the manure during decomposition. It is further contemplated that the odor reducing composition of the invention chemically reacts with at least some of the numerous odorous components found in manure.

Odors emanating during decomposition of manure may persist for as many as seven days depending on the temperature, amount of wind, and amount of humidity. Surprisingly, under moderate conditions, mild temperatures, e.g., 50 to 65° F., low wind, e.g., 0 to 3 mph, and low humidity, e.g., 30 to 50% relative humidity, one application of the odor reducing composition of the invention will reduce the odor originating from the manure for seven days. Preferably, the odor reducing composition of the invention is applied to the manure every third day. Even more preferably, the odor reducing composition is applied to the manure every other day. In the event, however, the temperature is higher than 65° F., the wind is greater than 3 mph, and/or the humidity is greater than 50% relative humidity, additional applications of the odor reducing composition to the manure may be necessary or desired.

While the odor reducing composition works especially well at reducing odors of manure, it is to be understood that the term odorous substrate also includes any other solids found in areas occupied by livestock which may emit an offending odor as a result of contamination by manure and/or urine, for example cat litter boxes.

Further examples of odorous substrates include composts, animal feeds, and food wastes. "Animal feeds" is herein defined as any livestock feed, including silage and fermentation by-products such as spent mash from breweries and distilleries, often used as livestock feed. "Food wastes" is herein defined as beef, poultry, pork, fish and vegetable wastes resulting from food preparation in restaurants, including discarded, uneaten portions. Accordingly, "food wastes" includes the raw, uncooked, beef, poultry, pork, fish and vegetables, as well as the cooked beef, poultry, pork, fish and vegetables.

Other odorous substrates include odor-emitting sludge, including sewage sludge located in retaining basins or lagoons and sewage treatment tanks, and liquid garbage found at municipal dump sites. "Sewage sludge" is herein defined as any liquid based mixture containing, either alone or in combination, manure and other fecal matter, urine, plant and animal matter, and any other organic material normally found in municipal waste. Sewage sludge may also include aerobic and/or anaerobic bacteria.

Still other odorous substrates include baby and adult diapers, carpet, solid garbage found in municipal dump sites, solid surfaces and liquids in portable toilets and bathrooms, and any other odorous surface or liquid.

In a specific embodiment of the invention, the odor reducing composition of the invention may be included in the form of a liquid in a "squirt" bottle, e.g., an atomizer, to reduce the odors of odorous substrates such as kitchen garbage, bathroom surfaces, any other odors created by various liquid, solid and gaseous wastes, by "squirting" the odor reducing composition onto the odorous substrate. The odor reducing composition of the invention may also include a liquid carrier, such as water, or a solid carrier such as capsules. For example, in a specific embodiment, the banana plant extract is blended with a solid carrier, such as water soluble capsules, which preferably dissolves when it is contacted with liquids, to be applied to odorous substrates such as liquids in portable toilets, septic tanks, fountains and ponds, retaining basins, lagoons, and sewage treatment tanks. Another specific embodiment of the invention is a cat litter, including pellets made from a solid carrier such as clay or some other inert material with banana plant extract blended in with the carrier.

Another specific embodiment of the invention, is an odor reducing composition that includes banana plant extract with a solid carrier such as a powder or gel, for application on human skin to reduce body odor. It can also be in granular or pellet form to be applied to a dry odorous substrate surface, such as carpet and furniture, to remove odors from the dry surface. In a specific embodiment, the pellets containing the odor reducing composition are broadcast over the area of the carpet containing the offending odors. The pellets are allowed to remain on the carpet for a period of time necessary for the odor to be reduced. The pellets are then removed from the carpet by vacuuming. In a further specific embodiment, water may be sprinkled slightly over the carpet while the pellets containing the odor reducing composition are in contact with the carpet. The water activates the pellets by releasing the odor reducing composition into the air where it may be absorbed by the carpet, and reduces odors emanating from the carpet. The carpet is then allowed to dry and then the carpet can be vacuumed to remove the pellets containing the odor reducing composition.

Another specific embodiment of the invention is an odor reducing composition including a banana plant extract and being formed into a pellet, wherein the pellets may also be broadcast over an area, such as the inside of a barn or any other area occupied by livestock, and designed to activate, and reduce odors, when the odorous substrate, such as urine or manure, is contacted with the pellet. The pellet is activated when the moisture from the manure or urine contacts the pellet. The moisture dissolves the pellet, thereby releasing the odor reducing composition. This specific embodiment works especially well in adult and baby diapers. For example, the pellets containing the odor reducing composition are placed inside the diapers. Once urine or feces contacts the pellets, the odor reducing composition is released and the odor emanating from the diaper due to the urine or feces is reduced. Also, the odor reducing composition may be incorporated into the diaper material itself. Thus, another specific embodiment of the invention includes a disposable diaper material that includes banana plant extract.

In yet another specific embodiment of this invention, an odor reducing composition that includes banana plant extract is applied orally to reduce odors emanating from and through the biological processes of animals, including human beings. Specifically, the odor reducing composition may include a biodegradable carrier, such as a capsule, which is easily digested by animals. The carrier may also be water or other liquid which is drunk by the animal, or the carrier may be in solid form, such as a biscuit or other food which is fed to the animal. The carrier containing the odor reducing composition may then be ingested by humans or animals. Once inside the digestive tract of the animal, the carrier is digested by the digestive system of the animal and the odor reducing composition is released. After the odor reducing composition is released, any odors emanating from the digestive tract of the animals which may be released from the digestive tract are reduced. In the case of human beings, the odor reducing composition can be chewing gum with an effective amount of banana plant extract.

In still another specific embodiment of the invention, the odor reducing composition is in liquid form and has not been diluted after its isolation. That odor reducing composition is applied to organic and inorganic solids containing manure and urine in areas occupied by livestock by spraying a thin coating of the odor reducing composition over the areas contaminated by the manure and urine. The odor reducing composition may be reapplied as necessary or desired to reduce the odor of the area occupied by the livestock.

In yet another embodiment of the invention, the odor reducing composition is applied to ponds, fountains, and sewage sludge found in retaining basins, lagoons, and sewage treatment tanks, and other odorous substrates which have a primarily liquid consistency. The odor reducing composition is preferably initially applied to these odorous substrates in an amount of from at least about 0.5% to 15% based upon the volume of the odorous substrate. Preferably, the odor reducing composition is initially applied to the odorous substrate in an amount of at least about 0.5% to 10% based upon the volume of the odorous substrate. The odor reducing composition may then be reapplied when necessary in an amount of from about 0.5% to 5% based upon the weight of the odorous substrate. Preferably, the odor reducing composition is reapplied to the odorous substrate in an amount of about 1% based upon the volume of the odorous substrate.

In still another specific embodiment of the invention, the odor reducing composition is applied to compost, food wastes and animal feeds by spraying a thin coating of the odor reducing composition over the surface of the compost, food wastes and animal feeds. The compost, food wastes and animal feeds may then be agitated, shifted, turned, stirred, or moved in such a way that the areas of the compost, food wastes and animal feeds not covered by the initial spraying of the odor reducing composition may be exposed and the odor reducing composition may be applied to those areas. The odor reducing composition may then be reapplied as necessary or desired to reduce the odor of the compost, food wastes and animal feeds.

In yet another specific embodiment, the invention is directed to an odor reducing composition that includes an odor reducing agent. "Odor reducing agent" is herein defined as the active ingredient in the banana plant extract, i.e., the chemical compound in the banana plant extract that reduces or removes odor. It is contemplated that the odor reducing agent may be found in the banana plant material in both its natural state, i.e., when the banana plant is growing, and may also be found in the banana plant material after harvesting and prior to separation of the banana plant extract from the banana plant material. Yet prior to its isolation as part of the banana plant extract, the odor reducing agent is in a sense "trapped" within the banana plant material, not capable of, or recognized as, being effectively used for reducing odors. Odor reducing agents also include any synthetically developed chemical composition having the same odor-reducing properties as the active odor reducing ingredient in the banana plant extract, which can be identified by any known method of isolating such compounds and testing for odor reduction.

In a still another specific embodiment of the invention, an odor reducing composition is formed by combining 300 grams (78.64 weight percent) water, 80 grams (20.97 weight percent) banana plant material, and 1.5 grams (0.39 weight percent) sodium hydroxide to form a banana plant mixture. The mixture is processed to form a banana plant pulp mixture. The banana plant pulp mixture is heated at a temperature of 212° F. for two and one-half hours to form a banana plant extract mixture having a banana plant extract portion and a banana plant residue portion. The banana plant extract mixture is passed through a colander screen to separate the banana plant extract portion of the banana plant extract mixture from the banana plant residue portion of the banana plant extract mixture. After it cools, the banana plant extract portion can be applied to manure or other fecal matter in an amount sufficient to completely coat the odorous substrate, resulting in a decrease in odor.

It is to be understood that the invention is not limited to the exact materials or embodiments shown and described, as obvious modifications and equivalents will be apparent to one skilled in the art who has read the contents of this patent. For example, as discussed above, the banana plant extract may be synthetically formed. Further, an odor reducing composition including the banana plant extract may include additional additives depending upon the type of odorous substrate to which the odor reducing composition will be applied. Also, the odor reducing composition may be applied to any solid or liquid odorous substrate in the manners described herein, or by any other method known in art. Additionally, the odor reducing composition may be applied to the various odorous substrates other than manure in the same manner that the odor reducing composition is applied to manure. Accordingly, the invention is therefore to be defined only by the scope of the appended claims, and equivalents thereof.

What is claimed is:

1. A method of reducing the odor of an odorous substrate comprising applying to the odorous substrate an odor reducing composition comprising banana plant extract.

2. The method of claim 1, wherein the odorous substrate includes manure, urine, or fecal matter and the odor is from the manure, urine, or fecal matter.

3. The method of claim 2, wherein the odor reducing composition is applied to the manure by spraying it onto the outer surface of the manure.

4. The method of claim 1, wherein the odorous substrate includes sewage sludge and the odor is from the sewage sludge.

5. The method of claim 4, wherein the odor reducing composition is applied to the sewage sludge in an amount of from about 0.5% to about 15% based on the volume of the sewage sludge.

6. The method of claim 1, wherein the odorous substrate is selected from the group consisting of manure, urine, sewage sludge, hay, straw, grass, soil, compost, carpet, animal feeds, diapers, garbage, food wastes, ponds, fountains, and septic tanks.

7. A method of reducing the odor of an odorous substrate by applying to the odorous substrate an odor reducing composition comprising banana plant extract, the method comprising the steps of:

(a) providing an odorous substrate; and (b) applying to the odorous substrate an odor reducing composition comprising banana plant extract, wherein the odor reducing composition comprising banana plant extract is formed by the steps of providing a banana plant material; and removing liquid banana plant extract from the banana plant material to form the odor reducing composition.

8. A method of reducing the odor of an odorous substrate by applying an odor reducing composition comprising banana plant extract to the odorous substrate, comprising the steps of:

(a) providing an odorous substrate; and (b) applying to the odorous substrate an odor reducing composition comprising banana plant extract in an amount sufficient to reduce the odor of the odorous substrate, wherein the odor reducing composition comprising banana plant extract is formed by the steps of providing a banana plant material; and removing liquid banana plant extract from the banana plant material to form the odor reducing composition.

9. A method of reducing the odor of an odorous substrate by applying an odor reducing composition comprising banana plant extract to the odorous substrate, comprising the steps of:

(a) providing an odorous substrate; and (b) applying to the odorous substrate an odor reducing composition comprising banana plant extract wherein the odor reducing composition comprising banana plant extract is formed by the steps of providing a banana plant material; processing the banana plant material to form a banana plant pulp; combining the banana plant pulp with water and an alkali metal hydroxide to form a banana plant pulp mixture; heating the banana plant pulp mixture to provide a banana plant extract mixture having a banana plant extract portion and a banana plant residue portion; and separating the banana plant extract portion of the banana plant extract mixture from the banana plant residue portion of the banana plant extract mixture to form an odor reducing composition comprising banana plant extract.

10. The method of claim 9, wherein the alkali metal hydroxide is sodium hydroxide.

11. A method for forming an odor reducing composition, comprising the steps of:

(a) providing a banana plant material;

(b) combining the banana plant material with water to form an aqueous banana plant material;

(c) increasing the alkalinity of the aqueous banana plant material to form a banana plant mixture; and (d) heating the banana plant mixture to form an odor reducing composition comprising the banana plant extract.

12. The method of claim 11, wherein the alkalinity is increased by adding an alkali metal hydroxide.

13. The method of claim 12, wherein the alkali metal hydroxide is sodium hydroxide.

14. The method of claim 11, wherein the banana plant mixture has a pH of from at least about 9 to about 14.

15. A method of forming an odor reducing composition, comprising the steps of:

(a) providing a banana plant material;

(b) combining the banana plant material with water and an alkali metal hydroxide to form a banana plant mixture; and (c) heating the banana plant mixture to form an odor reducing composition comprising the banana plant extract.

16. The method of claim 15, wherein the alkali metal hydroxide is sodium hydroxide.

17. A method of forming an odor reducing composition, comprising the steps of:

(a) providing a banana plant material;

(b) processing the banana plant material to form a banana plant pulp;

(c) combining the banana plant pulp with water and an alkali metal hydroxide to form a banana plant pulp mixture;

(d) heating the banana plant pulp mixture to provide a banana plant extract mixture having a banana plant extract portion and a banana plant residue portion; and (e) separating the banana plant extract portion of the banana plant extract mixture from the banana plant residue portion of the banana plant extract mixture to form an odor reducing composition comprising banana plant extract.

18. A method of forming an odor reducing composition, comprising the steps of:

(a) providing a banana plant material;

(b) grinding the banana plant material to form a banana plant pulp;

(c) combining the banana plant pulp with water and an alkali metal hydroxide to form a banana plant pulp mixture;

(d) heating the banana plant pulp mixture at a temperature of at least about 80 to about 212° F. for a period of time sufficient to provide banana plant extract mixture having a banana plant extract portion and a banana plant residue portion; and (e) separating the banana plant extract portion of the banana plant extract mixture from the banana plant residue portion of the banana plant extract mixture to form an odor reducing composition comprising banana plant extract.

19. The method of claim 18, wherein the banana plant pulp mixture is heated at a temperature of at least about 100° F. for at least about 1 to about 3 hours.

20. An odor reducing composition comprising a banana plant extract.

21. The odor reducing composition of claim 20, wherein the odor reducing composition includes a biostat.

22. The odor reducing composition of claim 21, wherein the biostat is glutaraldehyde.

23. The odor reducing composition of claim 20, wherein the odor reducing composition includes an inorganic phosphate compound.

24. The odor reducing composition of claim 23, wherein the inorganic phosphate compound is dibasic sodium phosphate.

25. An odor reducing composition comprising banana plant extract, wherein the odor reducing composition comprising banana plant extract is formed by the steps of providing a banana plant material; combining the banana plant material with water and an alkali metal hydroxide to form a banana plant mixture; and heating the banana plant mixture to form an odor reducing composition comprising the banana plant extract.

26. The odor reducing composition of claim 25, wherein the alkali metal hydroxide is sodium hydroxide.

27. An odor reducing composition comprising banana plant extract, wherein the odor reducing composition comprising banana plant extract is formed by the steps of providing a banana plant material; processing the banana plant material to form banana plant pulp; combining the banana plant pulp with water and an alkali metal hydroxide to form a banana plant pulp mixture; heating the banana plant pulp mixture to provide a banana plant extract mixture having a banana plant extract portion and a banana plant residue portion; and separating the banana plant extract portion of the banana plant extract mixture from the banana plant residue portion of the banana plant extract mixture to form an odor reducing composition comprising banana plant extract.

* * * * *